(12) United States Patent
Loscalzo et al.

(10) Patent No.: US 6,489,290 B2
(45) Date of Patent: *Dec. 3, 2002

(54) ANTIPLATELET AGENT

(75) Inventors: Joseph Loscalzo, Dover, MA (US); Aida Inbal, Hod-Hasharon (IL)

(73) Assignee: Trustees of Boston University, Boston, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/381,261

(22) PCT Filed: Mar. 27, 1998

(86) PCT No.: PCT/US98/06092

§ 371 (c)(1), (2), (4) Date: Dec. 7, 1999

(87) PCT Pub. No.: WO98/42753

PCT Pub. Date: Oct. 1, 1998

(65) Prior Publication Data

US 2002/0123457 A1 Sep. 5, 2002

Related U.S. Application Data

(60) Provisional application No. 60/046,981, filed on Mar. 27, 1997.

(51) Int. Cl.[7] .................. A61K 38/00; A61K 38/16; C07K 17/00
(52) U.S. Cl. ................. 514/2; 514/8; 514/12; 530/324; 530/345; 530/380; 530/383; 530/395; 435/69.6
(58) Field of Search ............... 514/2, 8, 12; 530/324, 530/345, 380, 383, 395; 435/69.6

(56) References Cited

U.S. PATENT DOCUMENTS 5,321,127 A * 6/1994 Handin ................. 530/383
5,344,783 A   9/1994 Scarborough et al. ...... 436/501
5,593,876 A * 1/1997 Stamler et al. ............. 435/188

OTHER PUBLICATIONS

Marks et al., *J. Clin. Invest.*, vol. 96, pp. 2630–2638, 1995.*
Jackson et al., *The Journal of Biological Chemistry*, vol. 269, No. 43, pp. 27093–27099, Oct. 1994.*
Matsushita et al., *The Journal of Biological Chemistry*, vol. 270, No. 22, pp. 13406–13414, Jun. 1995.*
Mancuso et al., J. Biol. Chem.; 264 (33): 19514–19527 (1989).
Gold et al., Circulation, 83 (Supplement IV): IV–26—IV–40 (1991).
Inbal et al.; Thrombosis and Haemostasis, 70 (6): 1058–1062 (1993).
Gurevitz et al.; Arteriosclerosis, Thrombosis and Vascular Biology, 18: 200–207 (1998).
Inbal et al.; Blood, 94(5): 1693–1700 (1999).
Leadley Jr. et al., Journal of Pharmacological and Toxicological Methods, 43: 101–116 (2000).
Lankhof et al, Blood, 89 (8) :2766–2772 (Apr. 15, 1997).

* cited by examiner

Primary Examiner—Karen Cochrane Carlson
Assistant Examiner—Abdel A. Mohamed
(74) Attorney, Agent, or Firm—Hale and Dorr LLP

(57) ABSTRACT

This invention combines the unique antiplatelet effects of S-nitrosothiols and the antiadhesive properties of fragments of von Willebrand (vWF) in the A1 domain to provide unique molecules that exploit both of these properties. Preferred molecules comprise a fragment of A1 (Ala 444-Asn 730) in which arginine at position 545 is replaced by cysteine (the most frequent von Willebrand disease type 2*b* mutation) that has been discovered to impair platelet adhesion, and to inhibit an antithrombotic activity in vivo. This cysteine residue may be S-nitrosated to produce a novel molecule that has the potential for impairing platelet adhesion as well as activation/aggregation, and such molecules form the basis of a novel therapeutic method for impairing platelet responses following vascular injury or in other thrombotic disorders according to this invention.

15 Claims, No Drawings

SEQUENCE LISTING

<160> NUMBER OF SEQ ID NOS: 3

<210> SEQ ID NO 1
<211> LENGTH: 2813
<212> TYPE: PRT
<213> ORGANISM: Homo sapiens

<400> SEQUENCE: 1

```
Met Ile Pro Ala Arg Phe Ala Gly Val Leu Leu Ala Leu Ala Leu Ile
1               5                   10                  15

Leu Pro Gly Thr Leu Cys Ala Glu Gly Thr Arg Gly Arg Ser Ser Thr
            20                  25                  30

Ala Arg Cys Ser Leu Phe Gly Ser Asp Phe Val Asn Thr Phe Asp Gly
        35                  40                  45

Ser Met Tyr Ser Phe Ala Gly Tyr Cys Ser Tyr Leu Leu Ala Gly Gly
    50                  55                  60

Cys Gln Lys Arg Ser Phe Ser Ile Ile Gly Asp Phe Gln Asn Gly Lys
65                  70                  75                  80

Arg Val Ser Leu Ser Val Tyr Leu Gly Glu Phe Phe Asp Ile His Leu
                85                  90                  95

Phe Val Asn Gly Thr Val Thr Gln Gly Asp Gln Arg Val Ser Met Pro
            100                 105                 110

Tyr Ala Ser Lys Gly Leu Tyr Leu Glu Thr Glu Ala Gly Tyr Tyr Lys
        115                 120                 125

Leu Ser Gly Glu Ala Tyr Gly Phe Val Ala Arg Ile Asp Gly Ser Gly
    130                 135                 140

Asn Phe Gln Val Leu Leu Ser Asp Arg Tyr Phe Asn Lys Thr Cys Gly
145                 150                 155                 160

Leu Cys Gly Asn Phe Asn Ile Phe Ala Glu Asp Asp Phe Met Thr Gln
                165                 170                 175

Glu Gly Thr Leu Thr Ser Asp Pro Tyr Asp Phe Ala Asn Ser Trp Ala
            180                 185                 190

Leu Ser Ser Gly Glu Gln Trp Cys Glu Arg Ala Ser Pro Pro Ser Ser
        195                 200                 205

Ser Cys Asn Ile Ser Ser Gly Glu Met Gln Lys Gly Leu Trp Glu Gln
    210                 215                 220

Cys Gln Leu Leu Lys Ser Thr Ser Val Phe Ala Arg Cys His Pro Leu
225                 230                 235                 240

Val Asp Pro Glu Pro Phe Val Ala Leu Cys Glu Lys Thr Leu Cys Glu
                245                 250                 255

Cys Ala Gly Gly Leu Glu Cys Ala Cys Pro Ala Leu Leu Glu Tyr Ala
            260                 265                 270
```

-continued

```
Arg Thr Cys Ala Gln Glu Gly Met Val Leu Tyr Gly Trp Thr Asp His
        275                 280                 285

Ser Ala Cys Ser Pro Val Cys Pro Ala Gly Met Glu Tyr Arg Gln Cys
    290                 295                 300

Val Ser Pro Cys Ala Arg Thr Cys Gln Ser Leu His Ile Asn Glu Met
305                 310                 315                 320

Cys Gln Glu Arg Cys Val Asp Gly Cys Ser Cys Pro Glu Gly Gln Leu
                325                 330                 335

Leu Asp Glu Gly Leu Cys Val Glu Ser Thr Glu Cys Pro Cys Val His
            340                 345                 350

Ser Gly Lys Arg Tyr Pro Pro Gly Thr Ser Leu Ser Arg Asp Cys Asn
        355                 360                 365

Thr Cys Ile Cys Arg Asn Ser Gln Trp Ile Cys Ser Asn Glu Glu Cys
    370                 375                 380

Pro Gly Glu Cys Leu Val Thr Gly Gln Ser His Phe Lys Ser Phe Asp
385                 390                 395                 400

Asn Arg Tyr Phe Thr Phe Ser Gly Ile Cys Gln Tyr Leu Leu Ala Arg
                405                 410                 415

Asp Cys Gln Asp His Ser Phe Ser Ile Val Ile Glu Thr Val Gln Cys
            420                 425                 430

Ala Asp Asp Arg Asp Ala Val Cys Thr Arg Ser Val Thr Val Arg Leu
        435                 440                 445

Pro Gly Leu His Asn Ser Leu Val Lys Leu Lys His Gly Ala Gly Val
    450                 455                 460

Ala Met Asp Gly Gln Asp Val Gln Leu Pro Leu Leu Lys Gly Asp Leu
465                 470                 475                 480

Arg Ile Gln His Thr Val Thr Ala Ser Val Arg Leu Ser Tyr Gly Glu
                485                 490                 495

Asp Leu Gln Met Asp Trp Asp Gly Arg Gly Arg Leu Leu Val Lys Leu
            500                 505                 510

Ser Pro Val Tyr Ala Gly Lys Thr Cys Gly Leu Cys Gly Asn Tyr Asn
        515                 520                 525

Gly Asn Gln Gly Asp Asp Phe Leu Thr Pro Ser Gly Leu Ala Glu Pro
    530                 535                 540

Arg Val Glu Asp Phe Gly Asn Ala Trp Lys Leu His Gly Asp Cys Gln
545                 550                 555                 560

Asp Leu Gln Lys Gln His Ser Asp Pro Cys Ala Leu Asn Pro Arg Met
                565                 570                 575

Thr Arg Phe Ser Glu Glu Ala Cys Ala Val Leu Thr Ser Pro Thr Phe
            580                 585                 590

Glu Ala Cys His Arg Ala Val Ser Pro Leu Pro Tyr Leu Arg Asn Cys
        595                 600                 605

Arg Tyr Asp Val Cys Ser Cys Ser Asp Gly Arg Glu Cys Leu Cys Gly
    610                 615                 620

Ala Leu Ala Ser Tyr Ala Ala Ala Cys Ala Gly Arg Gly Val Arg Val
625                 630                 635                 640

Ala Trp Arg Glu Pro Gly Arg Cys Glu Leu Asn Cys Pro Lys Gly Gln
                645                 650                 655

Val Tyr Leu Gln Cys Gly Thr Pro Cys Asn Leu Thr Cys Arg Ser Leu
            660                 665                 670

Ser Tyr Pro Asp Glu Glu Cys Asn Glu Ala Cys Leu Glu Gly Cys Phe
        675                 680                 685

Cys Pro Pro Gly Leu Tyr Met Asp Glu Arg Gly Asp Cys Val Pro Lys
```

-continued

```
        690                 695                 700
Ala Gln Cys Pro Cys Tyr Tyr Asp Gly Glu Ile Phe Gln Pro Glu Asp
705                 710                 715                 720

Ile Phe Ser Asp His His Thr Met Cys Tyr Cys Glu Asp Gly Phe Met
                725                 730                 735

His Cys Thr Met Ser Gly Val Pro Gly Ser Leu Leu Pro Asp Ala Val
                740                 745                 750

Leu Ser Ser Pro Leu Ser His Arg Ser Lys Arg Ser Leu Ser Cys Arg
                755                 760                 765

Pro Pro Met Val Lys Leu Val Cys Pro Ala Asp Asn Leu Arg Ala Glu
770                 775                 780

Gly Leu Glu Cys Thr Lys Thr Cys Gln Asn Tyr Asp Leu Glu Cys Met
785                 790                 795                 800

Ser Met Gly Cys Val Ser Gly Cys Leu Cys Pro Pro Gly Met Val Arg
                805                 810                 815

His Glu Asn Arg Cys Val Ala Leu Glu Arg Cys Pro Cys Phe His Gln
                820                 825                 830

Gly Lys Glu Tyr Ala Pro Gly Glu Thr Val Lys Ile Gly Cys Asn Thr
                835                 840                 845

Cys Val Cys Arg Asp Arg Lys Trp Asn Cys Thr Asp His Val Cys Asp
850                 855                 860

Ala Thr Cys Ser Thr Ile Gly Met Ala His Tyr Leu Thr Phe Asp Gly
865                 870                 875                 880

Leu Lys Tyr Leu Phe Pro Gly Glu Cys Gln Tyr Val Leu Val Gln Asp
                885                 890                 895

Tyr Cys Gly Ser Asn Pro Gly Thr Phe Arg Ile Leu Val Gly Asn Lys
                900                 905                 910

Gly Cys Ser His Pro Ser Val Lys Cys Lys Arg Val Thr Ile Leu
                915                 920                 925

Val Glu Gly Gly Glu Ile Glu Leu Phe Asp Gly Glu Val Asn Val Lys
                930                 935                 940

Arg Pro Met Lys Asp Glu Thr His Phe Glu Val Val Glu Ser Gly Arg
945                 950                 955                 960

Tyr Ile Ile Leu Leu Leu Gly Lys Ala Leu Ser Val Val Trp Asp Arg
                965                 970                 975

His Leu Ser Ile Ser Val Val Leu Lys Gln Thr Tyr Gln Glu Lys Val
                980                 985                 990

Cys Gly Leu Cys Gly Asn Phe Asp  Gly Ile Gln Asn Asn  Asp Leu Thr
                995                 1000                1005

Ser Ser  Asn Leu Gln Val Glu  Asp Pro Val Asp  Phe Gly Asn
            1010                1015                1020

Ser Trp  Lys Val Ser Ser Gln  Cys Ala Asp Thr Arg  Lys Val Pro
            1025                1030                1035

Leu Asp  Ser Ser Pro Ala Thr  Cys His Asn Asn Ile  Met Lys Gln
            1040                1045                1050

Thr Met  Val Asp Ser Ser Cys  Arg Ile Leu Thr Ser  Asp Val Phe
            1055                1060                1065

Gln Asp  Cys Asn Lys Leu Val  Asp Pro Glu Pro Tyr  Leu Asp Val
            1070                1075                1080

Cys Ile  Tyr Asp Thr Cys Ser  Cys Glu Ser Ile Gly  Asp Cys Ala
            1085                1090                1095

Cys Phe  Cys Asp Thr Ile Ala  Ala Tyr Ala His Val  Cys Ala Gln
            1100                1105                1110
```

-continued

```
His Gly Lys Val Val Thr Trp Arg Thr Ala Thr Leu Cys Pro Gln
    1115                1120                1125
Ser Cys Glu Glu Arg Asn Leu Arg Glu Asn Gly Tyr Glu Cys Glu
    1130                1135                1140
Trp Arg Tyr Asn Ser Cys Ala Pro Ala Cys Gln Val Thr Cys Gln
    1145                1150                1155
His Pro Glu Pro Leu Ala Cys Pro Val Gln Cys Val Glu Gly Cys
    1160                1165                1170
His Ala His Cys Pro Pro Gly Lys Ile Leu Asp Glu Leu Leu Gln
    1175                1180                1185
Thr Cys Val Asp Pro Glu Asp Cys Pro Val Cys Glu Val Ala Gly
    1190                1195                1200
Arg Arg Phe Ala Ser Gly Lys Lys Val Thr Leu Asn Pro Ser Asp
    1205                1210                1215
Pro Glu His Cys Gln Ile Cys His Cys Asp Val Val Asn Leu Thr
    1220                1225                1230
Cys Glu Ala Cys Gln Glu Pro Gly Gly Leu Val Val Pro Pro Thr
    1235                1240                1245
Asp Ala Pro Val Ser Pro Thr Thr Leu Tyr Val Glu Asp Ile Ser
    1250                1255                1260
Glu Pro Pro Leu His Asp Phe Tyr Cys Ser Arg Leu Leu Asp Leu
    1265                1270                1275
Val Phe Leu Leu Asp Gly Ser Ser Arg Leu Ser Glu Ala Glu Phe
    1280                1285                1290
Glu Val Leu Lys Ala Phe Val Val Asp Met Met Glu Arg Leu Arg
    1295                1300                1305
Ile Ser Gln Lys Trp Val Arg Val Ala Val Val Glu Tyr His Asp
    1310                1315                1320
Gly Ser His Ala Tyr Ile Gly Leu Lys Asp Arg Lys Arg Pro Ser
    1325                1330                1335
Glu Leu Arg Arg Ile Ala Ser Gln Val Lys Tyr Ala Gly Ser Gln
    1340                1345                1350
Val Ala Ser Thr Ser Glu Val Leu Lys Tyr Thr Leu Phe Gln Ile
    1355                1360                1365
Phe Ser Lys Ile Asp Arg Pro Glu Ala Ser Arg Ile Ala Leu Leu
    1370                1375                1380
Leu Met Ala Ser Gln Glu Pro Gln Arg Met Ser Arg Asn Phe Val
    1385                1390                1395
Arg Tyr Val Gln Gly Leu Lys Lys Lys Lys Val Ile Val Ile Pro
    1400                1405                1410
Val Gly Ile Gly Pro His Ala Asn Leu Lys Gln Ile Arg Leu Ile
    1415                1420                1425
Glu Lys Gln Ala Pro Glu Asn Lys Ala Phe Val Leu Ser Ser Val
    1430                1435                1440
Asp Glu Leu Glu Gln Gln Arg Asp Glu Ile Val Ser Tyr Leu Cys
    1445                1450                1455
Asp Leu Ala Pro Glu Ala Pro Pro Pro Thr Leu Pro Pro His Met
    1460                1465                1470
Ala Gln Val Thr Val Gly Pro Gly Leu Leu Gly Val Ser Thr Leu
    1475                1480                1485
Gly Pro Lys Arg Asn Ser Met Val Leu Asp Val Ala Phe Val Leu
    1490                1495                1500
```

-continued

```
Glu Gly Ser Asp Lys Ile Gly Glu Ala Asp Phe Asn Arg Ser Lys
1505                1510                1515

Glu Phe Met Glu Val Ile Gln Arg Met Asp Val Gly Gln Asp
1520                1525                1530

Ser Ile His Val Thr Val Leu Gln Tyr Ser Tyr Met Val Thr Val
1535                1540                1545

Glu Tyr Pro Phe Ser Glu Ala Gln Ser Lys Gly Asp Ile Leu Gln
1550                1555                1560

Arg Val Arg Glu Ile Arg Tyr Gln Gly Gly Asn Arg Thr Asn Thr
1565                1570                1575

Gly Leu Ala Leu Arg Tyr Leu Ser Asp His Ser Phe Leu Val Ser
1580                1585                1590

Gln Gly Asp Arg Glu Gln Ala Pro Asn Leu Val Tyr Met Val Thr
1595                1600                1605

Gly Asn Pro Ala Ser Asp Glu Ile Lys Arg Leu Pro Gly Asp Ile
1610                1615                1620

Gln Val Val Pro Ile Gly Val Gly Pro Asn Ala Asn Val Gln Glu
1625                1630                1635

Leu Glu Arg Ile Gly Trp Pro Asn Ala Pro Ile Leu Ile Gln Asp
1640                1645                1650

Phe Glu Thr Leu Pro Arg Glu Ala Pro Asp Leu Val Leu Gln Arg
1655                1660                1665

Cys Cys Ser Gly Glu Gly Leu Gln Ile Pro Thr Leu Ser Pro Ala
1670                1675                1680

Pro Asp Cys Ser Gln Pro Leu Asp Val Ile Leu Leu Leu Asp Gly
1685                1690                1695

Ser Ser Ser Phe Pro Ala Ser Tyr Phe Asp Glu Met Lys Ser Phe
1700                1705                1710

Ala Lys Ala Phe Ile Ser Lys Ala Asn Ile Gly Pro Arg Leu Thr
1715                1720                1725

Gln Val Ser Val Leu Gln Tyr Gly Ser Ile Thr Thr Ile Asp Val
1730                1735                1740

Pro Trp Asn Val Val Pro Glu Lys Ala His Leu Leu Ser Leu Val
1745                1750                1755

Asp Val Met Gln Arg Glu Gly Gly Pro Ser Gln Ile Gly Asp Ala
1760                1765                1770

Leu Gly Phe Ala Val Arg Tyr Leu Thr Ser Glu Met His Gly Ala
1775                1780                1785

Arg Pro Gly Ala Ser Lys Ala Val Val Ile Leu Val Thr Asp Val
1790                1795                1800

Ser Val Asp Ser Val Asp Ala Ala Ala Asp Ala Ala Arg Ser Asn
1805                1810                1815

Arg Val Thr Val Phe Pro Ile Gly Ile Gly Asp Arg Tyr Asp Ala
1820                1825                1830

Ala Gln Leu Arg Ile Leu Ala Gly Pro Ala Gly Asp Ser Asn Val
1835                1840                1845

Val Lys Leu Gln Arg Ile Glu Asp Leu Pro Thr Met Val Thr Leu
1850                1855                1860

Gly Asn Ser Phe Leu His Lys Leu Cys Ser Gly Phe Val Arg Ile
1865                1870                1875

Cys Met Asp Glu Asp Gly Asn Glu Lys Arg Pro Gly Asp Val Trp
1880                1885                1890

Thr Leu Pro Asp Gln Cys His Thr Val Thr Cys Gln Pro Asp Gly
```

-continued

```
         1895                1900                1905

Gln Thr Leu Leu Lys Thr His Arg Val Asn Cys Asp Arg Gly Leu
1910                1915                1920

Arg Pro Ser Cys Pro Asn Ser Gln Ser Pro Val Lys Val Glu Glu
1925                1930                1935

Thr Cys Gly Cys Arg Trp Thr Cys Pro Cys Val Cys Thr Gly Ser
1940                1945                1950

Ser Thr Arg His Ile Val Thr Phe Asp Gly Gln Asn Phe Lys Leu
1955                1960                1965

Thr Gly Ser Cys Ser Tyr Val Leu Phe Gln Asn Lys Glu Gln Asp
1970                1975                1980

Leu Glu Val Ile Leu His Asn Gly Ala Cys Ser Pro Gly Ala Arg
1985                1990                1995

Gln Gly Cys Met Lys Ser Ile Glu Val Lys His Ser Ala Leu Ser
2000                2005                2010

Val Glu Leu His Ser Asp Met Glu Val Thr Val Asn Gly Arg Leu
2015                2020                2025

Val Ser Val Pro Tyr Val Gly Gly Asn Met Glu Val Asn Val Tyr
2030                2035                2040

Gly Ala Ile Met His Glu Val Arg Phe Asn His Leu Gly His Ile
2045                2050                2055

Phe Thr Phe Thr Pro Gln Asn Asn Glu Phe Gln Leu Gln Leu Ser
2060                2065                2070

Pro Lys Thr Phe Ala Ser Lys Thr Tyr Gly Leu Cys Gly Ile Cys
2075                2080                2085

Asp Glu Asn Gly Ala Asn Asp Phe Met Leu Arg Asp Gly Thr Val
2090                2095                2100

Thr Thr Asp Trp Lys Thr Leu Val Gln Glu Trp Thr Val Gln Arg
2105                2110                2115

Pro Gly Gln Thr Cys Gln Pro Ile Leu Glu Glu Gln Cys Leu Val
2120                2125                2130

Pro Asp Ser Ser His Cys Gln Val Leu Leu Leu Pro Leu Phe Ala
2135                2140                2145

Glu Cys His Lys Val Leu Ala Pro Ala Thr Phe Tyr Ala Ile Cys
2150                2155                2160

Gln Gln Asp Ser Cys His Gln Glu Gln Val Cys Glu Val Ile Ala
2165                2170                2175

Ser Tyr Ala His Leu Cys Arg Thr Asn Gly Val Cys Val Asp Trp
2180                2185                2190

Arg Thr Pro Asp Phe Cys Ala Met Ser Cys Pro Pro Ser Leu Val
2195                2200                2205

Tyr Asn His Cys Glu His Gly Cys Pro Arg His Cys Asp Gly Asn
2210                2215                2220

Val Ser Ser Cys Gly Asp His Pro Ser Glu Gly Cys Phe Cys Pro
2225                2230                2235

Pro Asp Lys Val Met Leu Glu Gly Ser Cys Val Pro Glu Glu Ala
2240                2245                2250

Cys Thr Gln Cys Ile Gly Glu Asp Gly Val Gln His Gln Phe Leu
2255                2260                2265

Glu Ala Trp Val Pro Asp His Gln Pro Cys Gln Ile Cys Thr Cys
2270                2275                2280

Leu Ser Gly Arg Lys Val Asn Cys Thr Thr Gln Pro Cys Pro Thr
2285                2290                2295
```

-continued

```
Ala Lys Ala Pro Thr Cys Gly Leu Cys Glu Val Ala Arg Leu Arg
    2300                2305                2310
Gln Asn Ala Asp Gln Cys Cys Pro Glu Tyr Glu Cys Val Cys Asp
    2315                2320                2325
Pro Val Ser Cys Asp Leu Pro Pro Val Pro His Cys Glu Arg Gly
    2330                2335                2340
Leu Gln Pro Thr Leu Thr Asn Pro Gly Glu Cys Arg Pro Asn Phe
    2345                2350                2355
Thr Cys Ala Cys Arg Lys Glu Glu Cys Lys Arg Val Ser Pro Pro
    2360                2365                2370
Ser Cys Pro Pro His Arg Leu Pro Thr Leu Arg Lys Thr Gln Cys
    2375                2380                2385
Cys Asp Glu Tyr Glu Cys Ala Cys Asn Cys Val Asn Ser Thr Val
    2390                2395                2400
Ser Cys Pro Leu Gly Tyr Leu Ala Ser Thr Ala Thr Asn Asp Cys
    2405                2410                2415
Gly Cys Thr Thr Thr Thr Cys Leu Pro Asp Lys Val Cys Val His
    2420                2425                2430
Arg Ser Thr Ile Tyr Pro Val Gly Gln Phe Trp Glu Glu Gly Cys
    2435                2440                2445
Asp Val Cys Thr Cys Thr Asp Met Glu Asp Ala Val Met Gly Leu
    2450                2455                2460
Arg Val Ala Gln Cys Ser Gln Lys Pro Cys Glu Asp Ser Cys Arg
    2465                2470                2475
Ser Gly Phe Thr Tyr Val Leu His Glu Gly Glu Cys Cys Gly Arg
    2480                2485                2490
Cys Leu Pro Ser Ala Cys Glu Val Val Thr Gly Ser Pro Arg Gly
    2495                2500                2505
Asp Ser Gln Ser Ser Trp Lys Ser Val Gly Ser Gln Trp Ala Ser
    2510                2515                2520
Pro Glu Asn Pro Cys Leu Ile Asn Glu Cys Val Arg Val Lys Glu
    2525                2530                2535
Glu Val Phe Ile Gln Gln Arg Asn Val Ser Cys Pro Gln Leu Glu
    2540                2545                2550
Val Pro Val Cys Pro Ser Gly Phe Gln Leu Ser Cys Lys Thr Ser
    2555                2560                2565
Ala Cys Cys Pro Ser Cys Arg Cys Glu Arg Met Glu Ala Cys Met
    2570                2575                2580
Leu Asn Gly Thr Val Ile Gly Pro Gly Lys Thr Val Met Ile Asp
    2585                2590                2595
Val Cys Thr Thr Cys Arg Cys Met Val Gln Val Gly Val Ile Ser
    2600                2605                2610
Gly Phe Lys Leu Glu Cys Arg Lys Thr Thr Cys Asn Pro Cys Pro
    2615                2620                2625
Leu Gly Tyr Lys Glu Glu Asn Asn Thr Gly Glu Cys Cys Gly Arg
    2630                2635                2640
Cys Leu Pro Thr Ala Cys Thr Ile Gln Leu Arg Gly Gly Gln Ile
    2645                2650                2655
Met Thr Leu Lys Arg Asp Glu Thr Leu Gln Asp Gly Cys Asp Thr
    2660                2665                2670
His Phe Cys Lys Val Asn Glu Arg Gly Glu Tyr Phe Trp Glu Lys
    2675                2680                2685
```

-continued

```
Arg Val Thr Gly Cys Pro Pro Phe Asp Glu His Lys Cys Leu Ala
    2690            2695                2700
Glu Gly Gly Lys Ile Met Lys Ile Pro Gly Thr Cys Cys Asp Thr
    2705            2710                2715
Cys Glu Glu Pro Glu Cys Asn Asp Ile Thr Ala Arg Leu Gln Tyr
    2720            2725                2730
Val Lys Val Gly Ser Cys Lys Ser Glu Val Glu Val Asp Ile His
    2735            2740                2745
Tyr Cys Gln Gly Lys Cys Ala Ser Lys Ala Met Tyr Ser Ile Asp
    2750            2755                2760
Ile Asn Asp Val Gln Asp Gln Cys Ser Cys Cys Ser Pro Thr Arg
    2765            2770                2775
Thr Glu Pro Met Gln Val Ala Leu His Cys Thr Asn Gly Ser Val
    2780            2785                2790
Val Tyr His Glu Val Leu Asn Ala Met Glu Cys Lys Cys Ser Pro
    2795            2800                2805
Arg Lys Cys Ser Lys
    2810
```

<210> SEQ ID NO 2
<211> LENGTH: 8575
<212> TYPE: DNA
<213> ORGANISM: Homo sapiens

<400> SEQUENCE: 2

```
gcagctgaga gcatggccta gggtgggcgg caccattgtc cagcagctga gtttcccagg     60
gaccttggag atagccgcag ccctcatttg caggggaaga tgattcctgc agatttgcc    120
ggggtgctgc ttgctctggc cctcattttg ccagggaccc tttgtgcaga aggaactcgc    180
ggcaggtcat ccacggcccg atgcagcctt tcggaagtg acttcgtcaa cacctttgat    240
gggagcatgt acagctttgc gggatactgc agttacctcc tggcaggggg ctgccagaaa    300
cgctccttct cgattattgg ggacttccag aatggcaaga gagtgagcct ctccgtgtat    360
cttggggaat ttttgacat ccatttgttt gtcaatggta ccgtgacaca gggggaccaa    420
agagtctcca tgccctatgc ctccaaaggg ctgtatctag aaactgaggc tgggtactac    480
aagctgtccg gtgaggccta tggctttgtg gccaggatcg atggcagcgg caactttcaa    540
gtcctgctgt cagacagata cttcaacaag acctgcgggc tgtgtggcaa ctttaacatc    600
tttgctgaag atgactttat gacccaagaa gggaccttga cctcggaccc ttatgacttt    660
gccaactcat gggctctgag cagtggagaa cagtggtgtg aacgggcatc tcctcccagc    720
agctcatgca acatctcctc tgggaaatg cagaagggcc tgtgggagca gtgccagctt    780
ctgaagagca cctcggtgtt tgcccgctgc caccctctgg tggaccccga gccttttgtg    840
gccctgtgtg agaagacttt tgtgtgagtg tgctgggggc tggagtgcgc ctgccctgcc    900
ctcctggagt acgcccggac ctgtgcccag gagggaatgg tgctgtacgg ctggaccgac    960
cacagcgcgt gcagcccagt gtgccctgct ggtatggagt ataggcagtg tgtgtcccct   1020
tgcgccagga cctgccagag cctgcacatc aatgaaatgt gtcaggagcg atgcgtggat   1080
ggctgcagct gccctgaggg acagctcctg gatgaaggcc tctgcgtgga gagcaccgag   1140
tgtcctgcg tgcattccgg aaagcgctac cctcccggca cctccctctc tcgagactgc   1200
aacacctgca tttgccgaaa cagccagtgg atctgcagca atgaagaatg tccaggggag   1260
tgccttgtca caggtcaatc acacttcaag agctttgaca acagatactt caccttcagt   1320
```

-continued

| | | | | | |
|---|---|---|---|---|---|
| gggatctgcc | agtacctgct | ggcccgggat | tgccaggacc | actccttctc | cattgtcatt | 1380 |
| gagactgtcc | agtgtgctga | tgaccgcgac | gctgtgtgca | cccgctccgt | caccgtccgg | 1440 |
| ctgcctggcc | tgcacaacag | ccttgtgaaa | ctgaagcatg | ggcaggagt | tgccatggat | 1500 |
| ggccaggacg | tccagctccc | cctcctgaaa | ggtgacctcc | gcatccagca | tacagtgacg | 1560 |
| gcctccgtgc | gcctcagcta | cggggaggac | ctgcagatgg | actgggatgg | ccgcgggagg | 1620 |
| ctgctggtga | agctgtcccc | cgtctatgcc | gggaagacct | gcggcctgtg | tgggaattac | 1680 |
| aatggcaacc | agggcgacga | cttccttacc | ccctctgggc | tggcggagcc | ccgggtggag | 1740 |
| gacttcggga | acgcctggaa | gctgcacggg | gactgccagg | acctgcagaa | gcagcacagc | 1800 |
| gatccctgcg | ccctcaaccc | cgcgcatgacc | aggttctccg | aggaggcgtg | cgcggtcctg | 1860 |
| acgtccccca | cattcgaggc | ctgccatcgt | gccgtcagcc | cgctgcccta | cctgcggaac | 1920 |
| tgccgctacg | acgtgtgctc | ctgctcggac | ggccgcgagt | gcctgtgcgg | cgccctggcc | 1980 |
| agctatgccg | cggcctgcgc | ggggagaggc | gtgcgcgtcg | cgtggcgcga | gccaggccgc | 2040 |
| tgtgagctga | actgcccgaa | aggccaggtg | tacctgcagt | gcgggacccc | ctgcaacctg | 2100 |
| acctgccgct | ctctctctta | cccggatgag | gaatgcaatg | aggcctgcct | ggagggctgc | 2160 |
| ttctgccccc | cagggctcta | catggatgag | agggggggact | gcgtgcccaa | ggcccagtgc | 2220 |
| ccctgttact | atgacggtga | gatcttccag | ccagaagaca | tcttctcaga | ccatcacacc | 2280 |
| atgtgctact | gtgaggatgg | cttcatgcac | tgtaccatga | gtggagtccc | cggaagcttg | 2340 |
| ctgcctgacg | ctgtcctcag | cagtcccctg | tctcatcgca | gcaaaaggag | cctatcctgt | 2400 |
| cggccccccca | tggtcaagct | ggtgtgtccc | gctgacaacc | tgcgggctga | agggctcgag | 2460 |
| tgtaccaaaa | cgtgccagaa | ctatgacctg | gagtgcatga | gcatgggctg | tgtctctggc | 2520 |
| tgcctctgcc | ccccgggcat | ggtccggcat | gagaacagat | gtgtggccct | ggaaaggtgt | 2580 |
| ccctgcttcc | atcagggcaa | ggagtatgcc | cctggagaaa | cagtgaagat | tggctgcaac | 2640 |
| acttgtgtct | gtcgggaccg | gaagtggaac | tgcacagacc | atgtgtgtga | tgccacgtgc | 2700 |
| tccacgatcg | gcatgcccca | ctacctcacc | ttcgacgggc | tcaaataccc | gttccccggg | 2760 |
| gagtgccagt | acgttctggt | gcaggattac | tgcggcagta | accctgggac | ctttcggatc | 2820 |
| ctagtgggga | taagggatg | cagccacccc | tcagtgaaat | gcaagaaacg | ggtcaccatc | 2880 |
| ctggtggagg | gaggagagat | tgagctgttt | gacggggagg | tgaatgtgaa | gaggcccatg | 2940 |
| aaggatgaga | ctcactttga | ggtggtggag | tctggccggt | acatcattct | gctgctgggc | 3000 |
| aaagccctct | ccgtggtctg | ggaccgccac | ctgagcatct | ccgtggtcct | gaagcagaca | 3060 |
| taccaggaga | aagtgtgtgg | cctgtgtggg | aattttgatg | gcatccagaa | caatgacctc | 3120 |
| accagcagca | acctccaagt | ggaggaagac | cctgtggact | ttgggaactc | ctggaaagtg | 3180 |
| agctcgcagt | gtgctgacac | cagaaaagtg | cctctggact | catcccctgc | cacctgccat | 3240 |
| aacaacatca | tgaagcagac | gatggtggat | tcctcctgta | gaatccttac | cagtgacgtc | 3300 |
| ttccaggact | gcaacaagct | ggtggacccc | gagccatatc | tggatgtctg | catttacgac | 3360 |
| acctgctcct | gtgagtccat | tggggactgc | gcctgcttct | gcgacaccat | tgctgcctat | 3420 |
| gcccacgtgt | gtgcccagca | tggcaaggtg | gtgacctgga | ggacggccac | attgtgcccc | 3480 |
| cagagctgcg | aggagaggaa | tctccgggag | aacgggtatg | agtgtgagtg | gcgctataac | 3540 |
| agctgtgcac | ctgcctgtca | agtcacgtgt | cagcaccctg | agccactggc | ctgccctgtg | 3600 |
| cagtgtgtgg | agggctgcca | tgcccactgc | cctccaggga | aaatcctgga | tgagcttttg | 3660 |
| cagacctgcg | ttgaccctga | agactgtcca | gtgtgtgagg | tggctggccg | gcgttttgcc | 3720 |

```
tcaggaaaga aagtcacctt gaatcccagt gaccctgagc actgccagat tgccactgt   3780
gatgttgtca acctcacctg tgaagcctgc caggagccgg gaggcctggt ggtgcctccc   3840
acagatgccc cggtgagccc caccactctg tatgtggagg acatctcgga accgccgttg   3900
cacgatttct actgcagcag gctactggac ctggtcttcc tgctggatgg ctcctccagg   3960
ctgtccgagg ctgagtttga agtgctgaag gcctttgtgg tggacatgat ggagcggctg   4020
cgcatctccc agaagtgggt ccgcgtggcc gtggtggagt accacgacgg ctcccacgcc   4080
tacatcgggc tcaaggaccg gaagcgaccg tcagagctgc ggcgcattgc cagccaggtg   4140
aagtatgcgg gcagccaggt ggcctccacc agcgaggtct tgaaatacac actgttccaa   4200
atcttcagca gatcgaccg ccctgaagcc tcccgcatcg ccctgctcct gatggccagc   4260
caggagcccc aacggatgtc ccggaacttt gtccgctacg tccagggcct gaagaagaag   4320
aaggtcattg tgatcccggt gggcattggg ccccatgcca acctcaagca gatccgcctc   4380
atcgagaagc aggcccctga gaacaaggcc ttcgtgctga gcagtgtgga tgagctggag   4440
cagcaaaggg acgagatcgt tagctacctc tgtgaccttg ccctgaagc ccctcctcct   4500
actctgcccc cccacatggc acaagtcact gtgggcccgg ggctcttggg ggtttcgacc   4560
ctggggccca agaggaactc catggttctg gatgtgcgct tcgtcctgga aggatcggac   4620
aaaattggtg aagccgactt caacaggagc aaggagttca tggaggaggt gattcagcgg   4680
atggatgtgg ccaggacag catccacgtc acggtgctgc agtactccta catggtgacc   4740
gtggagtacc ccttcagcga ggcacagtcc aaaggggaca tcctgcagcg ggtgcgagag   4800
atccgctacc agggcggcaa caggaccaac actgggctgg ccctgcggta cctctctgac   4860
cacagcttct tggtcagcca gggtgaccgg gagcaggcgc ccaacctggt ctacatggtc   4920
accggaaatc ctgcctctga tgagatcaag aggctgcctg gagacatcca ggtggtgccc   4980
attggagtgg gccctaatgc caacgtgcag gagctggaga ggattggctg gcccaatgcc   5040
cctatcctca tccaggactt tgagacgctc ccccgagagg ctcctgacct ggtgctgcag   5100
aggtgctgct ccggagaggg gctgcagatc cccaccctct cccctgcacc tgactgcagc   5160
cagcccctgg acgtgatcct ctcctggat ggctcctcca gtttcccagc ttcttatttt   5220
gatgaaatga agagtttcgc caaggctttc atttcaaaag ccaatatagg gcctcgtctc   5280
actcaggtgt cagtgctgca gtatggaagc atcaccacca ttgacgtgcc atggaacgtg   5340
gtcccggaga aagcccattt gctgagcctt gtggacgtca tgcagcggga gggaggcccc   5400
agccaaatcg gggatgcctt gggctttgct gtgcgatact tgacttcaga aatgcatggt   5460
gccaggccgg gagcctcaaa ggcggtggtc atcctggtca cggacgtctc tgtggattca   5520
gtggatgcag cagctgatgc cgccaggtcc aacagagtga cagtgttccc tattggaatt   5580
ggagatcgct acgatgcagc ccagctacgg atcttggcag gccagcagg cgactccaac   5640
gtggtgaagc tccagcgaat cgaagacctc cctaccatgg tcaccttggg caattccttc   5700
ctccacaaac tgtgctctgg atttgttagg atttgcatgg atgaggatgg gaatgagaag   5760
aggcccgggg acgtctggac cttgccagac cagtgccaca ccgtgacttg ccagccagat   5820
ggccagacct tgctgaagac tcatcgggtc aactgtgacc ggggctgag gccttcgtgc   5880
cctaacagcc agtcccctgt taaagtggaa gagacctgtg ctgccgctg gacctgcccc   5940
tgcgtgtgca caggcagctc cactcggcac atcgtgacct ttgatgggca gaatttcaag   6000
ctgactggca gctgttctta tgtcctattt caaaacaagg agcaggacct ggaggtgatt   6060
```

```
ctccataatg gtgcctgcag ccctggagca aggcagggct gcatgaaatc catcgaggtg    6120
aagcacagtg ccctctccgt cgagctgcac agtgacatgg aggtgacggt gaatgggaga    6180
ctggtctctg ttccttacgt gggtgggaac atggaagtca acgtttatgg tgccatcatg    6240
catgaggtca gattcaatca ccttggtcac atcttcacat tcactccaca aaacaatgag    6300
ttccaactgc agctcagccc caagactttt gcttcaaaga cgtatggtct gtgtgggatc    6360
tgtgatgaga acggagccaa tgacttcatg ctgagggatg gcacagtcac cacagactgg    6420
aaaacacttg ttcaggaatg gactgtgcag cggccaggGc agacgtgcca gcccatcctg    6480
```

-continued

```
tgcaccaatg gctctgttgt gtaccatgag gttctcaatg ccatggagtg caaatgctcc    8520
cccaggaagt gcagcaagtg aggctgctgc agctgcatgg gtgcctgctg ctgcc         8575

<210> SEQ ID NO 3
<211> LENGTH: 18
<212> TYPE: PRT
<213> ORGANISM: Artificial Sequence
<220> FEATURE:
<223> OTHER INFORMATION: AR545C vWF fragment

<400> SEQUENCE: 3

Ala Glu Glu Ala Ser Gly Lys Lys Val Thr Leu Asn Pro Ser Asp Pro
1               5                   10                  15

Glu His
```

ANTIPLATELET AGENT

RELATED APPLICATIONS

This application is a §371 of PCT/US98/06092 filed Mar. 27, 1998, which claims priority to U.S. Provisional Application No. 60/046,981 filed Mar. 27, 1997.

BACKGROUND OF THE INVENTION

1. Field of the Invention

This invention is directed to anti-thrombotic therapy using novel anti-thrombotic agents. In particular, the anti-thrombotic agents are S-nitrosated polypeptides which bind to platelet receptor glycoprotein GPIb/IX.

2. Review of Related Art von Willebrand Factor and Platelet Function

During the past several years significant progress has been made in understanding the molecular aspects of platelet function with regard to both their role in normal hemostasis and the development of pathological vascular occlusion. The first event in normal primary hemostasis or development of arterial thrombosis is the binding (adhesion) of platelets to the subendothelium at sites of vascular injury. This first step occurs by binding of von Willebrand factor (vWF) to the platelet receptor glycoprotein Ib/IX (GPIb/IX) following its binding to components of exposed subendothelium. Thus, vWF acts as a "bridging" molecule between platelets and the vessel wall. As a consequence of vWF binding to GPIb, glycoprotein IIb/IIIa (GPIIb/IIIa) is activated through a complex signaling pathway leading to platelet aggregation mediated by fibrinogen or, under conditions of high shear stress, by vWF itself (Ruggeri, et al., 1982, *Proc. Natl. Acad. Sci. USA*, 79:6038–6041; Ruggeri, et al., 1983, *J. Clin. Invest.*, 72:1–12; Ikeda, et al., 1991, *J. Clin. Invest.*, 87:1234–1240). Furthermore, the binding of vWF to GPIb can mediate events that are associated with the effects of agonists like ADP and thrombin, such as activation of GPIIb/IIIa and support of platelet aggregation. This indicates that vWF serves as more than the "glue" that mediates platelet adhesion to the vessel wall but also induces and modulates other later steps of hemostasis and thrombogenesis.

vWF is a polymeric glycoprotein that circulates in plasma as a series of multimers with molecular weights ranging from $0.25 \times 10^6$ daltons to $20 \times 10^6$ daltons. In addition to its role in platelet adhesion, it carries and stabilizes factor VIII in the circulation (Sadler, 1991, *J Biol. Chem.*, 266:22777–22780). The vWF gene, located on chromosome 12, spans 178 kb and is interrupted by 51 introns (Ginsburg, et al., 1985, *Science*, 228:1401; Mancuso, et al., 1989, *J. Biol. Chem.*, 264:19514–19527.) vWF is synthesized from an 8.7 kb mRNA and is expressed in endothelial cells and megakaryocytes. Synthesis of vWF is a complex multistep process that results in the generation of a precursor protein, pre-pro-vWF (Meyer, et al., 1993, *Thromb. Haemost.*, 70:99–104).

This large molecule comprises a 22 amino acid (aa) signal peptide, as well as prov WF, which consists of a 741 aa propeptide and a 2050 aa mature subunit. These 250 kDa subunits assemble into multimers of up to 100 subunits (Wagner, 1990, *Annu. Rev. Cell Biol.*, 6:217–246). After dimerization by disulfide bonding at carboxyterminal domains in the endoplasmic reticulum, further multimerization takes place in the Golgi or post-Golgi compartments through disulfide linkages at amino-terminal domains.

In the blood vessel, vWF is constitutively secreted by endothelial cells. vWF is also stored within intracellular granules in both endothelial cells (Weibel-Palade bodies) and platelets (α-granules). These specialized granules release vWF in response to a variety of stimuli including vascular damage. The vWF stored within these granules contains larger multimers than those which are constitutively secreted by endothelial cells. These high-molecular-weight (HMW) multimers are more effective in platelet binding than smaller sized multimers (Gralnick, et al., 1981, *Blood*, 58:397–397; Federici, et al., 1989, *British Journal of Hematology*, 73:93–99); therefore, rapid release of stored vWF into the circulation may be particularly useful in the setting of vessel injury.

The pro vWF consists of four types of repeated domains (A to D) and has two disulfide loops: one is located between cys 509 and 695 in the A1 domain and the other between cys 923 and 1109 in the A3 domain (Meyer, et al., 1993, *Thromb. Haemost.*, 70:99–104). Progress has been made in identifying specific regions of the vWF subunit that are important for function. The A1 domain contains binding sites for GPIb, sulfatides, and heparin. Using proteolytic or recombinant fragments of vWF, the binding domain for GPIb has been located within the T116 fragments (aa 449–728) which overlaps the A1 loop (Fujimura, et al., 1986, *J. Biol. Chem.*, 261:381–385; Cruz, et al., 1993, *J. Biol. Chem.*, 268:21238–21245; Sugimoto, et al., 1991, *Biochemistry*, 30:5202–5209; Gralnick, et al., 1992, *Proc. Natl. Acad. Sci. USA*, 89:7880-4; Azuma, et al., 1991, J. Biol. Chem., 266:12342–12347; Pietu, et al., 1989, *Biochem. Biophys. Res. Commun.*, 164:1339–1347; Andrews, et al., 1989, *Biochemistry*, 28:8326–8336).

Under its native conformation, human vWF does not spontaneously interact with GPIb. The exposure of the GPI-binding site of vWF can be regulated by a series of physiological or non-physiological events. Most of these events appear to modify the structure and/or the conformation of the A1 region. The binding of vWF to the subendothelium, which spontaneously occurs via the T116 sequence (Denis, et al., 1993, *Arterioscler. Thromb.*, 13:398–406), is responsible for the subsequent exposure of the GPIb-binding site of vWF (Sakariassen, et al., 1979, *Nature*, 279:635–638). Similarly, collagen and heparin bind to vWF via sequences in the A1 loop (Mohri, et al., 1989, *J. Biol. Chem.*, 264:17361–17367) and modulate its interaction with GPIb. Binding of vWF to collagen promotes its interaction with GPIb while binding to heparin inhibits this interaction (Fressinaud, et al., 1988, *J. Lab. Clin. Med.*, 112(1):58–67; Sobel, et al., 1991, *J. Clin. Invest.*, 87:1787–1793; Savage, et al., 1992, *J. Biol. Chem.*, 267(16):11300–11306).

The interaction of vWF with non-physiologic modulators of its binding to GPIb also involves sequences close to or within the A1 loop. The immobilization of vWF on a plastic surface, for example, leads to platelet adhesion via GPIb (Berndt, et al., 1992, *Biochemistry*, 31:11144–11151). The interaction of vWF with ristocetin involves 474–488 and 692–708 sequences flanking the A1 loop, whereas botrocetin binds to four sequences within this loop (514–542, 539–553, 569–583 and 629–643) (Sugimoto, et al., 1991, *J. Biol. Chem.*, 266:18172–18178; Ginsburg, et al., 1993, *Thromb. Haemost.*, 69:177—184). The inhibition of vWF binding to GPIb by polyanionic compounds like aurin tricarboxylic acid (ATA) involves positively charged sequences of the A1 loop (Girma, et al., *Thromb. Haemost.*, 68:707–13, 1992). Finally, the GPIb-binding site can be achieved by the removal of the sialic acid residues from the carbohydrate side chains of vWF (Gralnick, et al., 1985, *J. Clin. Invest.*, 75:19–25). Since 9 of the 22 carbohydrate chains of vWF are within the T116 fragment but outside the A1 loop, the net local decrease of the negative charges may be responsible for the exposure of the GPIb-binding site.

Studies of patients with von Willebrand disease (vWD) have confirmed the role of the conformation of the A1 domain in the regulation of vWF binding to GPIb. vWF from patients with type 2B vWD is characterized by an increased capacity to bind to platelet GPIb. Mutations of this type have been identified within the 505–698 aa residues (Ginsburg, et al., *Thromb. Haemost.*, 69:177–84, 1993). The expression of recombinant, mutated vWF has confirmed the direct role of these mutations in the increased affinity of vWF for GPIb (Randi, et al., 1992, *J. Biol. Chem.*, 267:21187–21192; Inbal, et al., 1993, *Thromb. Haemost.*, 70:1058-1062; Cooney, et al., 1992, *Proc. Natl. Acad. Sci USA*, 89:2869–2872; Kroner, et al., 1992, *Blood*, 79:2048–2055).

Matsushita, et al. (1995, *J. Biol. Chem.*, 270:13406–13414) recently performed charged-to-alanine mutagenesis of the vWF A1 domain to examine the roles of specific charged residues in the interaction of vWF with platelet GPIb. By this approach, amino acid residues Glu596 and Lys599 appeared to be important in the interaction of vWF with platelet GPIb. Furthermore, alanine substitutions at Arg545, the site of the type 2b mutations studied by Inbal, et al. (1993, *Thromb. Haemost.*, 70:1058–62), and the segments between Glu496-Arg511 and Arg687-Glu689 resulted in spontaneous binding of vWF to GPIb. The striking distribution of positive and negative charges in distinct regions of the A1 domain suggests that intramolecular electrostatic interactions among these sites play a major role in the regulation of vWF binding to GPIb. An acidic segment, Asp252 and Asp287, of the GPIb a chain was identified as a binding site for vWF (Murata, et al., 1991, *J. Biol. Chem.*, 266:15474–15480).

Nitric Oxide and Platelet Function

An important determinant of the anti-thrombotic properties of the normal endothelium is its ability to inhibit platelet activation, adhesion, and aggregation. Two principal endothelial products account for these antiplatelet effects: prostacyclin and endothelium-derived relaxing factor (EDRF)/NO (Loscalzo, et al., 1996, in "Methods in Nitric Oxide Research," M. Feelisch and J. S. Stamler, editors, John Wiley & Sons, Ltd., Chichester. U.K., pp. 584–591). These substances act synergistically to inhibit platelet function, and do so through cAMP- and cGMP-dependent mechanisms, respectively (Loscalzo, et al., 1996). Importantly, while both prostacyclin and NO inhibit platelet activation and aggregation, only NO is effective as an inhibitor of platelet adhesion (deGraaf, et al., 1992, *Circ.*, 85:2284–2290). The importance of EDRF-mediated inhibition of platelet function in vivo is best illustrated by the observation that inhibition of NO synthesis can be accompanied by intravascular thrombosis (Shultz, et al., 1992, *J. Clin. Invest.*, 90:1718–1725, Freedman, et al., 1996, *J. Clin. Invest.*, 97:979–987). Inhibition of platelet function by NO can be potentiated by thiols (Loscalzo, et al., 1996), and this effect is probably a consequence of the formation of thionitrites or S-nitrosothiols (Loscalzo, et al., 1996). These NO adducts are potent platelet inhibitors that form in vivo and are probably responsible for stabilizing NO and for many of the biological effects attributed to NO directly in the vasculature (Loscalzo, et al., 1996). Previous work has shown that S-nitrosation of a protein avid for subendothelium (i.e., serum albumin) impairs platelet adhesion and smooth muscle proliferation following vascular injury (Marks, et al., 1995, *J. Clin. Invest.*, 96:2630–2638).

SUMMARY OF THE INVENTION

It is an object of this invention to provide new antithrombotic compositions which impair platelet activation and adhesion.

It is another object of this invention to provide a compound which competes with endogenous von Willebrand's Factor for binding to GPIb/IX but does not activate platelets upon binding to GPIb/IX.

It is another object of this invention to provide a method of treating an atherothrombotic disorder administering to patients new antithrombotic compositions which impair platelet activation and adhesion. These and other objects are met by one or more of the following embodiments.

In one embodiment, this invention provides a polypeptide which binds to platelet receptor glycoprotein Ib/IX (GPIb/IX) and competes with mature von Willebrand's Factor for binding to GPIb/IX, but does not activate platelets upon binding to GPIb/IX. The peptide of this invention contains at least one cysteine residue which is S-nitrosated. Preferably, the polypeptide according to this invention contains at least a portion of the sequence of the A1 domain of von Willebrand's factor. More preferably, the polypeptide according to this invention is polythiolated and a plurality of thiol groups are nitrosated.

In another embodiment, this invention provides a substantially pure polypeptide containing at least the amino acid sequence of von Willebrand's factor from Ala at position 444 to Asn at position 730 (corresponding to Ala 1207 to Asn 1493 of SE ID NO:1), but where the amino acid residue at position 545 is Cys (corresponding to amino acid residue 1308 of SEQ ID NO:1). Preferably, the polypeptide according to this embodiment has at least one cysteine residue which is S-nitrosated. More preferably, the polypeptide according to this embodiment is polythiolated and a plurality of thiol groups are nitrosated.

In yet another embodiment. this invention provides a method of treating a patient having an atherothrombotic disorder by administering to the patient a pharmaceutical composition containing a polypeptide which binds to platelet receptor glycoprotein Ib/IX (GPIb/IX) and competes with endogenous von Willebrand's Factor for binding to GPIb/IX, but does not activate platelets upon binding to GPIb/IX. Preferably the polypeptide used in this method contains at least one cysteine residue which is S-nitrosated. More preferably, the polypeptide according to this invention contains at least a portion of the sequence of the A1 domain of von Willebrand's factor. Even more preferably, the polypeptide according to this invention is polythiolated and a plurality of thiol groups are nitrosated.

The inventors have combined the unique antiplatelet effects of S-nitrosothiols and the antiadhesive properties of fragments of vWF in the A1 domain, thereby providing unique molecules that exploit both of these properties. One preferred molecule comprises a fragment of A1 (Ala 444-Asn 730) in which the arginine at position 545 is replaced by cysteine (the most frequent von Willebrand disease type 2b mutation) that has been shown by the inventors to impair platelet adhesion, and to exhibit antithrombotic activity in vivo. This cysteine residue is S-nitrosated, to produce a molecule that is denoted S-NO-AR545CvWF. This unique molecule has the potential for impairing platelet adhesion as well as activation/aggregation, and as such forms the basis of a novel therapeutic strategy for impairing platelet responses following vascular injury or in other thrombotic disorders.

DETAILED DESCRIPTION OF THE EMBODIMENTS

Antiplatelet Therapy

In both thrombosis and reclusion of coronary arteries, platelet adhesion is the initiating event. Thrombolytic therapy (streptokinase, tissue-type plasminogen activator) benefits patients who have suffered a myocardial infarction by reducing mortality and infarct size (Loscalzo, et al., 1996; Gruppo Italiano per lo Studio della Streptomachinasi nell'Infarto Miocardico, 1986, *Lancet*, 1:397–402; ISIS-2 (Second International Study of Infarct Survial) Collaborative Group, 1988, *J. Am. Coll. Cardiol.*, 12:3A–13A). However, the benefit is limited by incomplete reperfusion, a delayed recanalization time, and occurrence of thrombotic reclusion in up to 15% of cases (Van de Werf, et al., 1990, *British Med. J.*, 297:1374–1379; Colleen, 1990, *Ann. Intern. Med.*, 112:529–538: Colleen, et al., 1991, *Prig. Cardiovasc. Dis.*, 34:101–102). Importantly, thrombolytic therapy is also accompanied by increased platelet activation by the direct action of plasmin on the platelet, by the elaboration of thrombin through the action of plasmin in generating prothrombinase, and by the exposure of subendothelial collagen following lysis of the occlusive thrombus (Loscalzo, et al., 1995, *Thromb. Haemost.*, 74:291–293).

Since the first event in thrombogenesis is the recognition of vessel wall-bound vWF by platelets through the GPIb receptor, it is apparent that the selective inhibition of binding of endogenous vWF to GPIb as adjunctive therapy for thrombolysis would be an appropriate early intervention, likely to result in a beneficial anti-thrombotic effect. It was previously shown that the tryptic fragment of vWF of 52/48 kDa comprising residues Val449 and Lys728 inhibits the binding of native vWF to GPIb (Fujimura, et al., 1986, *J. Biol. Chem.*, 261:381–385). Moreover, the GPIb-binding domain of vWF expressed in *E. coli* has been shown to inhibit the binding of native vWF to GPIb (Sugimoto, et al., 1991, *Biochemistry*, 30:5202–5209), and unlike native vWF bound to GPIb, does so in the absence of any modulator. These previous studies provided the rationale for the use of a recombinant vWF fragment as an antiplatelet/antithrombotic agent. Indeed, recently, several fragments of vWF expressed in *E. coli* containing the A1 domain have been shown to bind to the platelet membrane GPIb receptor and inhibit the interaction of vWF with platelets (Gralnick, et al., 1992, *Proc. Natl. Acad. Sci. USA*, 89:7880–7884); Mohri, et al., 1993, *Peptides*, 14:125–129).

Experimental studies with VCL (Bio-Technology General, Inc.), another recombinant fragment of von Willebrand factor that spans from leu504 to lys728, showed delayed thrombus formation and reclusion in dogs (Yao, et al., 1994, *Circulation*, 89:2822–2828). This fragment was also shown to have local anti-thrombotic effects on nitrogen laser-induced thrombus formation in guinea pig mesenteric arteries without compromising general hemostasis and, importantly, without prolonging bleeding time (Azzam, et al., 1995, *Thromb. Haemost.*, 73:318–323).

The inventors have discovered that recombinant mutant vWF fragment AR545C can bind to the platelet surface receptor involved in adhesion and that this mutant fragment exhibits anti-thrombotic activity in vitro. The inventors have also discovered that nitric oxide congeners, such as S-nitroso-N-acetyl-L-cysteine and S-nitroso-serum albumin, have antiplatelet effects. Nitric oxide delivered by these S-nitrosothiols inhibits platelet function by a variety of interrelated mechanisms and, importantly, is a powerful inhibitor of platelet adhesion, a property not shared by the other potent endothelial product, prostacyclin.

Nitrosated (S-NO-AR545C), or polynitrosated mutant vWF fragment, (pS-NO-AR545C), provides targeted delivery of nitric oxide to the platelet through its S-nitrosothiol functional group(s). The targeted delivery of NO, based on AR545C binding to platelet glycoprotein Ib, will impair platelet activation and aggregation directly, an effect not manifest by the vWF fragments themselves, and thereby impairs platelet adhesion by two distinct mechanisms. These mechanisms at the very least are additives, but may also be synergistic, increasing the potency of the pharmacologic effects significantly.

The novel compounds of this invention represent a potential novel class of therapeutic agents useful for the treatment of atherothrombotic disorders. AR545C manifests its antithrombotic properties without prolonging the bleeding time in experimental animals. With the polynitrosated derivative, the toxic/therapeutic ratio (therapeutic index) for this class of antiplatelet agents will be significantly improved over existing agents.

Compounds of this invention are generally characterized in that they compete with von Willebrand factor for binding to platelet membrane protein GP Ib/IX. Generally, the compounds of this invention will not activate platelets upon binding to GP Ib. Additionally, compounds according to this invention contain one or more nitrosated thiol groups. Usually, the base compound prior to nitrosation will not activate platelets; however, so long as the nitrosated compound fails to activate platelets, the compound may be within the contemplation of this invention. Particular preferred compounds are polypeptides derived from the amino acid sequence of the A1 domain of von Willebrand's factor. Fragments of von Willebrand's factor which compete for binding to receptor protein GP Ib are described above, and these fragments are suitable starting points for the compounds of this invention. Where such peptide fragments are capable of binding GPIb but do not contain cysteine residues, thiol groups for nitrosation may be added by homocysteine thiolactone dervatization of epsilon- or alpha-amino groups through ester links by the methods of Benesch and Benesch (1958, *Proc. Natl. Acad. Sci. USA*, 44:848–853). Alternatively, analogs of the fragments may be prepared using recombinant DNA techniques by expression of a nucleic acid sequence corresponding to a portion of the von Willebrand sequence except for point mutation of one or more codons to encode cysteine residues in the expressed polypeptide.

The practice of the present invention employs, unless otherwise indicated, conventional molecular biology, microbiology, and recombinant DNA techniques within the skill of the art. Such techniques are well known to the skilled worker and are explained fully in the literature. See, e.g., Maniatis, Fritsch & Sambrook, "Molecular Cloning: A Laboratory Manual" (1982): "DNA Cloning: A Practical Approach," Volumes I and II (D. N. Glover, ed., 1985); "Oligonucleotide Synthesis" (M. J. Gait, ed., 1984); "Nucleic Acid Hybridization" (B. D. Hames & S. J. Higgins, eds., 1985); "Transcription and Translation" (B. D. Hames & S. J. Higgins, eds., 1984); "Animal Cell Culture" (R. I. Freshney, ed., 1986); "Immobilized Cells and Enzymes" (IRL Press, 1986): B. Perbal, "A Practical Guide to Molecular Cloning" (1984), and Sambrook, et al., "Molecular Cloning: a Laboratory Manual" (1989).

The polypeptide and DNA sequence of vWF is readily available to those skilled in the art, for instance in Genbank under accession No. X04385. The polypeptide sequence of vWF is shown in SEQ ID NO. 1, and the DNA sequence of vWF is shown in SEQ ID NO. 2. DNA segments or oligonucleotides having specific sequences can be synthesized chemically or isolated by one of several approaches. The basic strategies for identifying, amplifying and isolated desired DNA sequences as well as assembling them into larger DNA molecules containing the desired sequence domains in the desired order, are well known to those of ordinary skill in the art. See, e.g., Sambrook, et al., (1989); B. Perbal., (1984). Preferably, DNA segments corresponding to all or a portion of the vWF sequence may be isolated individually using the polymerase chain reaction (M. A. Innis, et al., "PCR Protocols: A Guide To Methods and Applications," Academic Press, 1990). A complete sequence may be assembled from overlapping oligonucleotides prepared by standard methods and assembled into a complete coding sequence. See, e.g., Edge (1981), *Nature,* 292:756; Nambair, et al. (1984), *Science,* 223:1299 Jay et al. (1984), *J. Biol. Chem.,* 259:6311.

The assembled sequence can be cloned into any suitable vector or replicon and maintained there in a composition which is substantially free of vectors that do not contain the assembled sequence. This provides a reservoir of the assembled sequence, and segments or the entire sequence can be extracted from the reservoir by excising from DNA in the reservoir material with restriction enzymes or by PCR amplification. Numerous cloning vectors are known to those of skill in the art, and the selection of an appropriate cloning vector is a matter of choice (see, e.g., Sambrook, et al., incorporated herein by reference). The construction of vectors containing desired DNA segments linked by appropriate DNA sequences is accomplished by techniques similar to those used to construct the segments. These vectors may be constructed to contain additional DNA segments, such as bacterial origins of replication to make shuttle vectors (for shuttling between prokaryotic hosts and mammalian hosts), etc.

Procedures for construction and expression of mutant proteins of defined sequence are well known in the art. A DNA sequence encoding a mutant form of vWF or a fragment thereof can be synthesized chemically or prepared from the wild-type sequence by one of several approaches, including primer extension, linker insertion and PCR (see, e.g., Sambrook, et at.). Mutants can be prepared by these techniques having additions, deletions and substitutions in the wild-type sequence. It is preferable to test the mutants to confirm that they are the desired sequence by sequence analysis and/or the assays described below. Mutant vWF fragments for testing may be prepared by placing the coding sequence for the polypeptide in a vector under the control of a promoter, so that the DNA sequence is transcribed into RNA and translated into protein in a host cell transformed by this (expression) vector. The mutant fragments may be produced by growing host cells transfected by an expression vector containing the coding sequence for the mutant under conditions whereby the polypeptide is expressed. The selection of the appropriate growth conditions is within the skill of the art.

Producing the Recombinant Peptide

Preferably, DNA from the selected clones should be subcloned into an expression vector, and the polypeptide expressed by cells transformed with the vector may be tested for immunoreactivity with antibodies against vWF or the polypeptide of this invention. Such subcloning is easily within the skill of the ordinary worker in the art in view of the present disclosure. The amino acid coding region of the DNA sequence for this invention may be longer or shorter than the coding region of vWF so long as the recombinant peptide expressed by the DNA sequence retains ability to bind GPIb. The preparation of selected clones which contain DNA sequences corresponding to all or part of the sequence of vWF may be accomplished by those of ordinary skill in the art using conventional molecular biology techniques along with the information provided in this specification and the vWF sequence as disclosed herein.

Where clones are selected from an expression library, selection may be accomplished by expressing the library sequences and detecting the expressed peptides immunologically. Clones are selected that express peptides which bind antibodies specific for vWF or which bind GPIb. These selection procedures are well known to those of ordinary skill in the art (see, e.g., Sambrook, et al.). Hybridization using a nucleic acid whose sequence corresponds to the sequence of vWF may be used to select clones corresponding to a portion of the vWF gene.

Cloning for Expression

Once a coding sequence for the desired polypeptide sequence has been prepared or isolated, it can be cloned into any suitable vector or replicon and thereby maintained in a composition which is substantially free of vectors that do not contain the coding sequence (e.g., free of other clones from the library). Numerous cloning vectors are known to those of skill in the art, and the selection of an appropriate cloning vector is a matter of choice (see, e.g., Sambrook, et al., incorporated herein by reference). The DNA sequences and DNA molecules of the present invention may be expressed using a wide variety of host/vector combinations. According to the present invention, the coding sequence is placed under the control of a promoter, ribosome binding site (for bacterial expression) and, optionally, an operator (collectively referred to herein as "control" elements), so that the DNA sequence is transcribed into RNA in the host cell transformed by a vector containing this expression construct. The coding sequence may or may not contain a signal peptide or leader sequence.

Of course, not all host/expression vector combinations function with equal efficiency in expressing the DNA sequences of this invention or in producing the polypeptides of this invention. However, a particular selection of a host/expression vector combination may be made by those skilled in the art. For example, the selection should be based on a balancing of a number of factors. These include compatibility of the host and vector, toxicity of the proteins encoded by the DNA sequence to the host, ease of recovery of the desired protein, expression characteristics of the DNA sequences and the expression control sequences operatively linked to them, biosafety, costs and the folding, form or any other necessary post-expression modifications of the desired protein. Preferably, the host cell will not express proteases which degrade the recombinant polypeptide of this invention.

Depending on the expression system and host selected, the protein is produced by growing host cells transformed by an expression vector containing the coding sequence for a polypeptide cross-reactive with the hpr gene product under conditions whereby the protein is expressed. The protein is then isolated from the host cells and purified. The selection of the appropriate growth conditions and recovery methods are within the skill of the art. Suitable expression vector and host cell systems are well known to those of ordinary skill in the art, and are taught, for instance, in Sambrook, et al., 1989. The peptide may be obtained by growing the transformed cells in culture under conditions wherein the cloned DNA is expressed. Depending on the expression vector chosen, the peptide may be expressed as a fusion protein or a mature protein which is secreted or retained intracellularly, or as an inclusion protein. The desired polypeptides can be recovered from the culture by well-known procedures, such as centrifugation, filtration, extraction, and the like, with or without cell rupture, depending on how the peptide was expressed. The crude aqueous solution or suspension may be enriched for the desired peptide by protein purification techniques well known to those skilled in the art.

Purified polypeptides prepared as described herein may be readily nitrosated by S-nitroso-glutathione using standard procedures of direct nitrosation or trans-S-nitrosation (Zhang, et al., 1996, *Meth. Neurosci.,* 31:41–46; Zhang, et al., 1996, *J. Biol. Chem.,* 271:14271–14279). Other procedures for nitrosating thiol groups on polypeptides which are know to those skilled in the art may also be used.

The skilled worker will of course confirm that molecules prepared according to this invention have the required properties of competitive binding to the GPIb platelet receptor in a manner which competes with vWF and does not activate platelets. Suitable assays are set forth in detail in the examples below, including inhibition of ristocetin-induced platelet aggregation, inhibition of platelet aggregation induced by ADP-thrombin, and inhibition of platelet adhesion in a flow model. Further confirmatory assays may include demonstration of clot lysis in a rabbit femoral thrombosis model (see Rudd, et al., 1992, *Circ. Res.,* 70:829–834) or radiolabeled platelet accretion model (see Marks, et al., 1995, *J. Clin. Invest.,* 96:2630–2638).

Anti-thrombotic molecules according to this invention provide a new mode of therapy for atherothrombotic arterial diseases and venous thrombotic diseases. Atherothrombotic arterial diseases within the contemplation of this invention include coronary artery disease, such as stable angina pectoris, acute coronary syndromes, such as unstable angina pectoris and acute myocardial infarction; cerebral vascular disease, including acute stroke and transient ischemic attack; mesenteric arterial disease; mesenteric ischemia "abdominal angina," and mesenteric infarction; as well as peripheral arterial disease, including acute peripheral arterial occlusion and intermittent claudication. Compounds of this invention are also useful during treatment of coronary artery disease, including anti-thrombotic therapy during coronary angioplasty, anti-thrombotic therapy during cardiopulmonary bypass, and limiting of platelet activation during ischemia reperfusion. Venous thrombotic diseases which may be treated according to this invention include deep venous thrombosis and pulmonary thromboembolism. These compounds are also useful in anti-thrombotic therapy for pulmonary hypertension.

Therapeutic compounds according to this invention are preferably formulated in pharmaceutical compositions containing the compound and a pharmaceutically acceptable carrier. The pharmaceutical composition may contain other components so long as the other components do not reduce the effectiveness of the compound according to this invention so much that the therapy is negated. Some other components may have independent therapeutic effects. Pharmaceutically acceptable carriers are well known, and one skilled in the pharmaceutical art can easily select carriers suitable for particular routes of administration (see, e.g., *Remington's Pharmaceutical Sciences,* Mack Publishing Co., Easton, Pa., 1985). The concentrations of the active agent in pharmaceutically acceptable carriers may range from 0.01 µg/ml to 500 µg/ml.

The pharmaceutical compositions containing any of the compounds of this invention may be administered by parenteral (subcutaneously, intramuscularly, intravenously, intraperitoneally, intrapleurally, intravesicularly or intrathecally), topical, oral, rectal, or nasal route, as necessitated by choice of drug and disease.

Dose and duration of therapy will depend on a variety of factors, including the therapeutic index of the drugs, disease type, patient age, patient weight, and tolerance of toxicity. Dose will generally be chosen to achieve serum concentrations from about 0.1 µg/ml to about 100 µg/ml. Preferably, initial dose levels will be selected based on their ability to achieve ambient concentrations shown to be effective in in-vitro models, such as that used to determine therapeutic index, and in-vivo models and in clinical trials, up to maximum tolerated levels. Standard clinical procedure prefers that chemotherapy be tailored to the individual patient and the systemic concentration of the chemotherapeutic agent be monitored regularly. The dose of a particular drug and duration of therapy for a particular patient can be determined by the skilled clinician using standard pharmacological approaches in view of the above factors. The response to treatment may be monitored by analysis of blood or body fluid levels of the compound according to this invention, measurement of activity if the compound or its levels in relevant tissues or monitoring disease state in the patient. The skilled clinician will adjust the dose and duration of therapy based on the response to treatment revealed by these measurements.

These compounds may also be applied locally or topically in gels, ointments, solutions, impregnated bandages, liposomes, or biodegradable microcapsules. Compositions or dosage forms for topical application may include solutions, lotions, ointments, creams, gels, suppositories, sprays, aerosols, suspensions, dusting powder, impregnated bandages and dressings, liposomes, biodegradable polymers, and artificial skin. Typical pharmaceutical carriers which make up the foregoing compositions include alginates, carboxymethylcellulose, methylcellulose, agarose, pectins, gelatins, collagen, vegetable oils, mineral oils, stearic acid, stearyl alcohol, petrolatum, polyethylene glycol, polysorbate, polylactate, polyglycolate, polyanhydrides, phospholipids, polyvinylpyrrolidone, and the like. For example, these compounds may be used to impede restenosis by application in a hydrogel at the time of angioplasty. A preferred strategy is to administer these compounds angioscopically in a suitable formulation.

A particularly preferred formulation for compounds according to this invention is in liposomes. Liposomes containing compounds according to this invention may be prepared by any of the methods known in the art for preparation of liposomes containing inclusions. Liposomes that are particularly suited for aerosol application to the lungs are described in International Patent Publication WO 93/12756, pages 25–29, incorporated herein by reference.

EXAMPLES

In order to facilitate a more complete understanding of the invention, a number of Examples are provided below. However, the scope of the invention is not limited to specific embodiments disclosed in these Examples, which are for purposes of illustration only.

Example 1

Production of vWF Fragments with Increased Affinity for Platelets

The vWF that contained the most frequent type 2b von Willebrand disease mutation—a substitution of arginine by cysteine at aa residue 545 (R545C)—has been expressed recombinantly (Inbal, et al., 1993, *Thromb. Haemost.,* 70:1058–1062). The recombinant R545CvWF protein exhibited an increased affinity for platelet GPIb. In order to study whether the increased binding of R545CvWF to platelets will remain within the truncated mutant vWF molecule after deletion of all the cDNA sequences except the putative GPIb binding domain, a recombinant fragment of vWF spanning from Ala 444 to Asn 730 containing the Arg545Cys mutation was constructed (Ala$^{444}$-Asn$^{730}$, named AR545CvWF).

Using PCR-directed mutagenesis (Shymala, et al., 1991, Gene, 97:1–6), a truncated vWF cDNA fragment was designed that contained the native coding sequence for aa 444-730 and an arginine-by-cysteine substitution at aa 545. This mutated, truncated plasmid, denoted pSVAR545C was constructed from the full length R545CvWF plasmid by deleting sequences before Ala 444 and introducing the stop codon after Asn 730. Two oligonucleotides that added an EcoR I restriction site at the 5' end of codon Ala 444 and at the 3' end of codon Asn 730 were employed for polymerase chain reaction (Shymala, et al., 1991, Gene, 97: 1–6). The amplified fragment underwent EcoRI digestion followed by cloning within the EcoRI digested expression vector pZEM229. Thus, the resultant mutated plasmid, pSVAR545C, contained a fragment of vWF which comprises domains D3, A1 an part of A2 and the Arg545Cys mutation within the A1 domain. The sequence of each construct was verified by direct sequencing as described previously (Inbal, et al., 1993, Thromb. Haemost., 70:1058–1062).

The recombinant wild type (pSUHvWF1) and mutated plasmid (pSVAR545C) were transfected in COS-7 cells by DEAE-dextran method as previously described (Inbal, et al., 1993, Thromb. Haemost., 70:1058–1062; Englander, et al., 1996, Blood, 87:2788–2794). The recombinant proteins, wild type and AR545CvWF, were concentrated by ultrafiltration (Centriprep-30, Centricon-30, Amicon, Inc.) and quantitated by a sandwich ELISA using 1:1000 rabbit anti-human vWF (Dakopatts A082) as the coating antibody and 1:5000 peroxidase-conjugated anti-vWF antibody (Dakopatts P226) as the detecting antibody (Inbal, et al., 1993, Thromb. Haemost., 70:1058–1062; Inbal, et al., 1993, Blood, 82:830–836). Western blot analysis of the recombinant AR545CvWF fragment using a monoclonal antibody that recognizes the A2 domain (36C4) disclosed a 116 kDa dimer that generated 52–48 kDa monomers upon reduction.

Example 2
Inhibition of Ristocetin-induced Platelet Aggregation by vWF Fragments GPIb binding to wild type or AR545CvWF was analyzed in the absence or presence of ristocetin as described by Inbal, et al. (1993, Thromb. Haemost., 70:1058–1062). In this method, various concentrations of either recombinant wild type vWF or AR545wVF fragments are incubated with formalin-fixed platelets (5×10$^8$/ml) for 15 min in a platelet aggregometer prior to the addition of 1 µg/ml vWF and 1 mg/ml ristocetin.

One microgram/ml of wild type or AR545CvWF was incubated with formalin-fixed platelets in the absence and presence of increasing concentrations of ristocetin. After 30 minutes of incubation, the bound platelet AR545CvWF complex was separated by centrifugation and the unbound vWF was quantitated by ELISA. In the absence of ristocetin, 60% of the AR545CvWF bound to platelets (spontaneous binding) and the binding increased to 80% at a ristocetin concentration of 1 mg/ml. This increase contrasts with that of either absent or very little binding of wild type to platelets in the absence or at low concentrations of ristocetin, respectively.

Example 3
Large Scale Production and Purification of the AR545CvWF Fragment

The recombinant vWF plasmid pSVAR545C was expressed in mammalian cells. The reason for choosing the mammalian transfection system is based on the fact that aa residues 445–507 that flank the A1 domain are glycosylated and the nonglycosylated E. coli derived material presents a neoantigenic site (Mohri, et al., 1993, Peptides, 14:125–129). Since the yield of COS-7 cell transfection was insufficient for the large scale production of the recombinant mutant vWF fragments, BHK cells were used.

Cell Culture and Expression of pSVAR545C

A thymidine kinase-deficient BHK cell line, BHK-570, was used as the host cell for the transfection experiments (Meijers et al., 1992, Blood, 79:1435–1440). Cells were grown in Dulbecco's modified Eagle medium (DMEM), 5% fetal calf serum (FSC), 50 µg/mL penicillin, 50 µg/mL streptomycin, and 100 µg/mL neomycin Beit Ha'emek, Israel) in a 5% CO$_2$ atmosphere at 37° C. For transfection, BHK-570 cells were plated at 1:15 split ratios in 90-mm plates (Falcon, Oxnard, Calif.) overnight and transfected for 4 hours in 10 mL of medium with 30 µg of plasmid precipitated with calcium phosphate. After a 1-minute shock in 15% glycerol in Tris-phosphate-buffered saline (25 mmol/L Tris-HCl, pH 7.4, 0.14 mol/L NaCl, 5 mmol/L KCl, 0.7 mmol/L CaCl$_2$, 0.5 mmol/L MgCl$_2$ and 0.6 mmol/L Na$_2$HPO), the cells were grown for 24 hours in normal medium. The cells were then subjected to selective medium containing 1 µmol/L methotrexate (Abic, Israel). The methotrexate concentration was increased gradually to 20 µmol/L, and the clones were picked and propagated. At confluence, the cells were washed twice in PBS and cultured in 8 ml of serum free Dulbecco's modified Eagle medium/per T-75 culture flask. Medium was collected after 24 hours, and EDTA, phenylmethylsulfonyl fluoride, leupeptin and pepstatin were added to final concentration of 100 µM, 100 µg/ml, 1 µg/ml, 1 µg/ml, respectively. Conditioned media was concentrated by ultrafiltration (Amicor Inc. Beverly, Calif., USA). Since the heparin binding site remained within the AR545C vWF fragment, for in vivo experiments the media was further purified on heparin affinity chromatography support (Ecomo-Pac® heparin cartridge, Bio Rad USA). The purity of the vWF fragment was verified by gel electrophoresis. The amount of vWF in conditioned medium was quantified by a sandwich ELISA using 1:100 rabbit anti-human vWF (Dakopatts A082) as the coating antibody and 1:1000 peroxidase-conjugated anti-vWF antibody (Dakopatts P226) as the detecting antibody. ELISAs were developed with O-phenylenediamine as the colorimetric substrate and quantitated at A$_{490}$ on an ELISA reader (Molecular Devices, USA). The amino-terminal amino acid sequence of the AR545C vWF fragment (SEQ ID NO. 3) was determined as a proof of identity using standard procedures. The first 18 aa are: A E E A S G K K V T L N P S D P E (SEQ ID NO. 3).

Ristocetin-induced Platelet Agglutination

Ristocetin-induced platelet agglutination was performed using lyophilized formalin-fixed platelets (Bio Data, Hartboro, Pa.) as described previously with slight modifications (Gralnick, et al., 1992, Proc. Natl. Acad. Sci. USA, 89:7880–7884). Various concentrations of AR545C vWF were incubated with the platelets (2×10$^8$ platelets/ml) for 15 min. in a platelet aggregometer PACKS-4, (Helena Laboratories, Beaumont, Tex.) at 37° C. prior to the addition of 25 µl of platelet poor plasma (PPP) as a source of vWF and 1 mg/ml ristocetin (Sigma, St. Louis, Mo.), and the percent agglutination was recorded. AR545C vWF inhibited ristocetin-induced platelet agglutination in a dose dependent manner with $IC_{50}$ of 0.80±0.04 μmol/L. The agglutination was completely abolished at 3 μmol/L of AR545C vWF.

Example 4
Anti-thrombotic Properties of AR545CvWF

Anti-thrombotic properties of the AR545CvWF fragment were analyzed using the rabbit femoral thrombosis model of Gold, et al. (1991, *Circulation*, 83:IV26–IV40). Briefly, a rabbit femoral artery was exposed and the vascular clamps were placed before and after the site of insertion of the superior epigastric artery (SEA). A cannula was inserted through SEA to induce thrombus. Distally the femoral artery was ligated to decrease the flow (measured by flow meter every 10 minutes) by 50%. The blood within the clamped segment was removed, the segment was traumatized by three compressions with blunt forceps to produce endothelial injury, and 100 μl of rabbit atrial whole blood plus 40 units of bovine thrombin were injected to generate thrombus. Fifteen minutes after thrombus formation, both clamps were withdrawn and no flow was recorded.

To evaluate the anti-thrombotic properties of AR545CvWF, one hundred microliters of AR545CvWF fragment (1 μg/ml) or mock transfected material (control) was injected through a cannula inserted within the superior epigastric artery, followed by a 450 μg/kg bolus of tissue-type plasminogen activator (t-PA) as previously described (Gold, et al., 1991). The following parameters were measured; 1) time to thrombus formation; 2) time to first reperfusion; 3) time to reocclusion; 4) rate of reperfusion; and 5) total patency time. Eighteen New Zealand white rabbits were included in the study. Nine received the mutated fragment (AR545CvWF) and nine served as control, receiving mock transfected material. The results of these studies showed that the time to first reperfusion was significantly shorter in the experimental group than in the control (60.6±17.3 minutes vs. 103.0±15.2 minutes, respectively, p=0.05). In addition, total patency time was also significantly increased in the group that received the mutated fragment compared with controls (175 minutes vs. 21 minutes, p=0.04). With this protocol, however, there was no significant difference in either the time to first reocclusion (p=0.62) or the reperfusion rate (p=0.15), suggesting further benefit may be obtained by additional injections of the fragment or continuous IV infusion after the bolus injection.

Example 5
Effect of Nitrosation on AR545CvWF

S-NO-AR545CvWF has been synthesized and examined for its antiplatelet effects, S-NO-AR545CvWF was prepared by incubating AR545CvWF with a 3-fold excess of S-nitroso-glutathione in phosphate-buffered saline or with a 1.3-fold excess of $NaNO_2$ in 1 mM HCl for 15 minutes at room temperature. Excess S-nitroso-glutathione or $NaNO_2$ was removed by molecular sieve chromatography using a Sephadex G-25 column. Polynitrosation was performed as described by Marks, et al. (1995, *Journal of Clinical Investigation*, 96:2630–2638); this procedure leads to incorporation of several S-NO groups per vWF fragment, and the resultant polynitrosated molecule is denoted pS-NO-AR545CvWF. The stoichiometry of S-nitrosation is determined using the Saville reaction (Saville, 1958. *Analyst*, 83:670–672).

Inhibition of Platelet Adhesion by AR545CvWF or S-NO-AR545CvWF

Platelet adhesion was assessed by determining the binding of platelets to endothelial cell monolayers or to extracellular matrix. Platelets were prepared from whole blood anticoagulated with 13 mM trisodium citrate and labeled with [$^{111}$In]oxine. Endothelial cell monolayers or extracellular matrix surfaces were washed twice with Tyrode's solution at 37 C. prior to the addition of 1 ml of labeled platelets (a total of $5\times10^8$ platelets) to each well. An agonist used to induce the release of EDRF from the endothelial cell monolayers (e.g., bradykinin, substance P or acetylcholine), or AR545CvWF or S-NO-AR545CvWF were added 1 minute prior to the addition of platelets. In the case of extracellular matrix surface, platelets were preincubated with an NO-containing solution of AR545CvWF or S-NO-AR545CvWF for 1 minute prior to the addition of platelets. The platelets were incubated with the monolayers of matrix for 10 minutes at 37 C., after which the incubation suspension was removed, and the endothelial cells or matrix washed twice with Tyrode's solution at 37 C. The radioactivity remaining associated with the monolayers or matrix is indicative of adherent platelets, and it was liberated with 0.5% Triton X-100 and quantified in a γ-counter. The effect of nitrosated fragments of vWF can be measured using the procedure of Example 2.

The nitrosated fragment S-NO-AR545CvWF completely inhibited ristocetin-induced platelet agglutination at 0.8 μM while the non-nitrosated fragment caused only 50% inhibition at the same concentration. S-NO-AR545CvWF inhibited ristocetin-dependent platelet agglutination and also inhibited platelet adhesion in a flow chamber, and it did so 2.5-fold more potently than did the parent compound that was not nitrosated.

Platelet Aggregation Using ADP and Thrombin

Importantly, S-NO-AR545CvWF also inhibits platelet aggregation in response to flow or in response to collagen or ADP, a property not shared by AR545CvWF. In some of the experiments the formalin-fixed platelets and purified vWF were substituted with platelet-rich plasma, and inhibition of ristocetin-induced aggregation was recorded by aggregometry. Platelet-rich plasma was diluted with platelet-poor plasma to give a final concentration of $1.0\times10^5$ platelets/μl. Platelet aggregation was induced with 0.05 mM ADP or with thrombin (2.5 units/ml) plus L-glycyl-L-prolyl-L-arginyl-L-proline (1.5 mM final concentration) to prevent fibrin polymerization (Loscalzo, et al., 1986). Aggregation was monitored at 37 C. while stirring (900 rpm) using a dualchannel aggregometer (Payton Associates, Inc., Buffalo). Aggregation was quantified by measuring the maximal rate of change in light transmittance.

The nitrosated fragment abolished ADP-induced platelet aggregation at 2.5 μM, while the same concentration of non-nitrosated fragment still resulted in 60% aggregation.

Platelet Interaction with Extracellular Matrix (ECM) in the Cone and Plate Device (CAP)

Platelet adhesion and aggregation on ECM was tested. Briefly, 0.25 ml of citrated whole blood was placed on an ECM covered plate and subjected to arterial flow conditions (sheer rate of 1300 $sec^{-1}$) for 2 minutes by applying a cone and plate device, specially designed for this test. The sample was then washed and stained with May Grunwald Stain (stran for peripheurl blood cells including platelets) and the degree of adhesion (expressed a percent of surface coverage—SC) and aggregation (expressed as average size of the objects—AS) was determined using an image analysis system (Galai, Beit Ha'emek, Israel). Blood samples were preincubated at room temperature for 50 minutes with various concentrations of the nitrosated or non-nitrosated AR545C vWF and the extent of adhesion and aggregation was recorded. Using the CAP device, 0.2 μM of the nitrosated fragment completely inhibited platelet aggregation and decreased the adhesion by 62%.

The nitrosated fragment exhibits significant antiplatelet properties, as demonstrated by a variety of tests fo platelet adhesion and aggregation.

For purposes of clarity of understanding, the foregoing invention has been described in some detail by way of illustration and example in conjunction with specific embodiments, although other aspects, advantages and modifications will be apparent to those skilled in the art to which the invention pertains. The foregoing description and examples are intended to illustrate, but not limit the scope of the invention. Modifications of the abovedescribed modes for carrying out the invention that are apparent to persons of skill in medicine, pharmacology, and/or related fields are intended to be within the scope of the invention, which is limited only by the appended claims.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

What is claimed is:

1. An isolated nitrosated polypeptide comprising an amino acid sequence of SEQ ID NO:1 from Ala 1207 to Asn 1493 wherein the amino acid at position 1308 is an S-nitrosated cysteine.

2. The polypeptide of claim 1, wherein the polypeptide contains a plurality of thiol groups and the plurality of thiol groups are nitrosated.

3. The polypeptide of claim 1, wherein the polypeptide binds to a platelet receptor glycoprotein Ib/IX, competes with von Willebrand's Factor for binding to the glycoprotein Ib/IX, and does not activate platelets upon binding to the glycoprotein Ib/IX.

4. A method for inhibiting at least one of platelet adhesion, platelet aggregation and platelet activation in a patient in need thereof comprising administering an effective amount of the polypeptide of claim 1 for a time and under conditions effective for inhibiting at least one of platelet adhesion, platelet aggregation and platelet activation.

5. A method for treating an atherothrombotic arterial disease by inhibiting at least one of platelet adhesion, platelet aggregation and platelet activation in a patient in need thereof comprising administering an effective amount of the polypeptide of claim 1 for a time and under conditions effective to treat an atherothrombotic arterial disease by inhibiting at least one of platelet adhesion, platelet aggregation and platelet activation.

6. The method of claim 5, wherein the atherothrombotic arterial disease is a coronary artery disease, a cerebral vascular disease, a mesenteric arterial disease or a peripheral arterial disease.

7. A method for treating a venous thrombotic disease by inhibiting at least one of platelet adhesion, platelet aggregation and platelet activation in a patient in need thereof comprising administering an effective amount of the polypeptide of claim 1 for a time and under conditions effective to treat a venous thrombotic disease by inhibiting at least one of platelet adhesion, platelet aggregation and platelet activation.

8. The method of claim 7, wherein the venous thrombotic disease is a deep venous thrombosis or a pulmonary thromboembolism.

9. A composition comprising the nitrosated polypeptide of claim 1 and a pharmaceutically acceptable carrier.

10. The composition of claim 9, wherein the concentration of the nitrosated polypeptide is about 0.01 µg/ml to about 500 µg/ml.

11. A method for inhibiting at least one of platelet adhesion, platelet aggregation and platelet activation in a patient in need thereof comprising administering an effective amount of the composition of claim 9 for a time and under conditions effective for inhibiting at least one of platelet adhesion, platelet aggregation and platelet activation.

12. A method for treating an atherothrombotic arterial disease by inhibiting at least one of platelet adhesion, platelet aggregation and platelet activation in a patient in need thereof comprising administering an effective amount of the composition of claim 9 for a time and under conditions effective to treat an atherothrombotic arterial disease by inhibiting at least one of platelet adhesion, platelet aggregation and platelet activation.

13. The method of claim 12, wherein the atherothrombotic arterial disease is a coronary artery disease, a cerebral vascular disease, a mesenteric arterial disease or a peripheral arterial disease.

14. A method for treating a venous thrombotic disease by inhibiting at least one of platelet adhesion, platelet aggregation and platelet activation in a patient in need thereof comprising administering an effective amount of the composition of claim 9 for a time and under conditions effective to treat a venous thrombotic disease by inhibiting at least one of platelet adhesion, platelet aggregation and platelet activation.

15. The method of claim 14, wherein the venous thrombotic disease is a deep venous thrombosis or a pulmonary thromboembolism.

* * * * *